US012594351B2

(12) United States Patent     (10) Patent No.:   US 12,594,351 B2

Fernandez et al.     (45) Date of Patent:    Apr. 7, 2026

(54) METHODS FOR INCREASING SHELF-LIFE OF OPHTHALMIC PHARMACEUTICAL COMPOSITIONS

(71) Applicant: Harrow IP, LLC, Nashville, TN (US)

(72) Inventors: Ernesto Fernandez, San Diego, CA (US); William F. Wiley, Chagrin, OH (US); Dennis Elias Saadeh, Nashville, TN (US)

(73) Assignee: Harrow IP LLC, Nashville, TN (US)

( * ) Notice: Subject to any disclaimer, the term of this patent is extended or adjusted under 35 U.S.C. 154(b) by 736 days.

(21) Appl. No.: 17/881,092

(22) Filed: Aug. 4, 2022

(65) Prior Publication Data

US 2023/0050398 A1     Feb. 16, 2023

Related U.S. Application Data

(60) Provisional application No. 63/229,181, filed on Aug. 4, 2021.

(51) Int. Cl.

| *A61L 2/00* | (2006.01) |
|---|---|
| *A61K 9/00* | (2006.01) |
| *A61K 9/08* | (2006.01) |
| *A61K 31/196* | (2006.01) |
| *A61K 31/4709* | (2006.01) |
| *A61K 31/573* | (2006.01) |
| *A61L 2/04* | (2006.01) |
| *A61L 103/05* | (2026.01) |

(52) U.S. Cl.

CPC .............. *A61L 2/04* (2013.01); *A61K 9/0048* (2013.01); *A61K 9/08* (2013.01); *A61K 31/196* (2013.01); *A61K 31/4709* (2013.01); *A61K 31/573* (2013.01); *A61L 2103/05* (2026.01)

(58) Field of Classification Search

CPC ........................... A61K 31/573; A61L 2/0023

See application file for complete search history.

(56) References Cited

U.S. PATENT DOCUMENTS

| 2016/0175317 | A1* | 6/2016 | Shah | ...................... | A61K 47/26 |
|---|---|---|---|---|---|
| | | | | | 514/226.5 |
| 2018/0325854 | A1* | 11/2018 | Coulon | ................... | A61K 9/06 |
| 2021/0369728 | A1* | 12/2021 | Jesudian | .............. | A61K 31/542 |
| 2022/0062301 | A1* | 3/2022 | Shah | ...................... | A61K 47/26 |

FOREIGN PATENT DOCUMENTS

WO     2017192675 A1    11/2017

\* cited by examiner

*Primary Examiner* — Kevin Joyner

(74) *Attorney, Agent, or Firm* — Polsinelli PC

(57)      ABSTRACT

The present disclosure relates to methods for extending the shelf life of a sterile ophthalmic pharmaceutical composition.

13 Claims, No Drawings

METHODS FOR INCREASING SHELF-LIFE OF OPHTHALMIC PHARMACEUTICAL COMPOSITIONS

CROSS-REFERENCE TO RELATED APPLICATIONS

This application claims priority to U.S. Provisional Application No. 63/229,181, filed Aug. 4, 2021, the entire contents of which are incorporated by reference herein.

FIELD OF THE DISCLOSURE

The present disclosure relates generally to the field of pharmaceuticals and more specifically to the preparation of ophthalmic pharmaceutical compositions.

BACKGROUND

Post-operative care for patients recovering from ophthalmic procedures often includes administration of eye drops including multiple active ingredients to reduce pain, inflammation, and likelihood of infection. In some cases, each of these active ingredients is administered separately from the others. Additionally, to ensure that the active ingredients are absorbed properly, the active ingredients are administered about 15 minutes apart. This cumbersome process results in low patient adherence to post-operative instructions. One solution to this problem is to administer all of the active ingredients in one drop. Formulations including multiple active ingredients would have to remain stable for the duration of the patient's post-operative care. Thus, there is a need for ophthalmic formulations comprising multiple active ingredients that remain stable for long periods of storage and use.

SUMMARY OF THE DISCLOSURE

Described herein are methods for extending the shelf life of sterile, pharmaceutical ophthalmic compositions. The method includes autoclaving a first phase composition, autoclaving or sterile-filtering a second phase composition, and combining the first phase composition and the second phase composition aseptically. In some aspects, the autoclaving temperature is about 121° C., and the pressure is between about 15 and about 18 psi. In still further aspects, the autoclaving step takes place for about 30 minutes. The resulting composition has a shelf life of at least 90 days when stored at room temperature and a pH of between about 7.5 to about 9.0.

In some embodiments, the first phase composition comprises a steroid and at least one excipient. In some examples, the steroid includes prednisolone acetate and the at least one excipient may include sodium acetate, polyoxyethylene sorbitan monooleate, hypromellose, and combinations thereof.

In some embodiments, the second phase composition comprises a fluoroquinolone, a non-steroidal anti-inflammatory agent, and at least one excipient. In some examples, the fluoroquinolone includes moxifloxacin, the non-steroidal anti-inflammatory agent includes bromfenac, and the at least one excipient includes sodium phosphate, sodium metabisulfite, edetate disodium, boric acid, sodium borate, benzalkonium chloride, and combinations thereof.

In some embodiments, the pharmaceutical compositions prepared by the methods of the present disclosure may have a shelf life of at least about 120 days, 150 days, 180 days, 210 days, 240 days, 270 days, 300 days, or 365 days when stored at room temperature.

These, and other iterations and aspects of the invention are described in more detail below.

DETAILED DESCRIPTION

It is to be understood that this disclosure is not limited to the particular methods, compositions, or materials specified herein, but is extended to equivalents thereof as would be recognized by those ordinarily skilled in the relevant arts. It should also be understood that terminology employed herein is used for the purpose of describing particular embodiments only and is not intended to be limiting.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/mL to about 80 mg/mL" should also be understood to provide support for the range of "50 mg/mL to 80 mg/m L" The endpoint may also be based on the variability allowed by an appropriate regulatory body, such as the FDA, USP, etc.

As used herein, "comprises," "comprising," "containing," and "having" and the like can have the meaning ascribed to them in U.S. Patent Law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

As used herein, "room temperature" describes the temperature of an ambient environment with no particular measures taken to control temperature (e.g. refrigeration). As used herein, room temperature is from about 20° C. and about 30° C.; for example, about 25° C.

As used herein, "stable" and "stability" refer to the slow or lacking degradation of one or more active ingredients of a pharmaceutical composition. Stated another way, a stable composition is one in which one or more active ingredients have not degraded or decomposed over a period of time and the concentration of one or more active ingredients has not significantly changed over a period of time. Alternatively, or in addition, a stable composition has a pH that does not change significantly over time. For example, a stable composition's pH may not change by more than ±0.5 during the shelf-life of the composition.

As used herein, "potency" refers to the concentration of one or more active ingredients in a pharmaceutical composition in reference to the amount of the one or more active ingredients needed to produce a therapeutic effect. As a non-limiting example, a hypothetical pharmaceutical composition may require 1% (w/v) of an active ingredient to have a therapeutic effect. The hypothetical composition would lack potency if it only contained 0.1% (w/v) of the active ingredient. Generally, a stable composition is also a potent composition.

As used herein, "shelf life" refers to the time period wherein a pharmaceutical composition is stable, potent, and free of microbial contamination when stored at room temperature. As an example, a hypothetical composition has a shelf life of at least 90 days when the composition is stable, potent, and free of microbial contamination after at least 90 days of storage at room temperature.

I. METHODS

Described herein is a method for extending the shelf life of a sterile ophthalmic pharmaceutical composition. The method includes autoclaving a first phase composition, autoclaving or sterile-filtering a second phase composition, and then combining aseptically the first phase composition and the second phase composition. The method results in an ophthalmic pharmaceutical composition that has superior stability over similar ophthalmic pharmaceutical compositions prepared by combining all ingredients together and autoclaving the entire composition at once.

The method may substantially increase the shelf-life of the ophthalmic pharmaceutical composition. In some embodiments, the ophthalmic pharmaceutical composition may remain stable for about 90 to about 365 days when stored at room temperature. In some embodiments, the ophthalmic pharmaceutical composition may remain stable for about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days when stored at room temperature. In some embodiments, the ophthalmic pharmaceutical composition may remain stable for at least about 90, 100, 110, 120, 130, 140, 150, 160, 170, 180, 190, 200, 210, 220, 230, 240, 250, 260, 270, 280, 290, 300, 310, 320, 330, 340, 350, 360, or at least about 365 days when stored at room temperature. In preferred embodiments, the ophthalmic pharmaceutical composition may remain stable for greater than 365 days when stored at room temperature.

The concentration of active pharmaceutical ingredients in the ophthalmic pharmaceutical composition after storage at room temperature for about 90 to 365 days may be at least about 90% to about 110% (w/v) of the concentration of active ingredients that were initially present in the ophthalmic pharmaceutical formulation. In some additional aspects, the concentration of active ingredients in the ophthalmic pharmaceutical composition after storage at room temperature for about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of active ingredients that was initially present in the ophthalmic pharmaceutical composition. In still further aspects, the concentration of active ingredients in the ophthalmic pharmaceutical composition after storage at room temperature for at least about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of active ingredients that was initially present in the ophthalmic pharmaceutical composition. In preferred embodiments, the concentration of active pharmaceutical ingredients in the ophthalmic pharmaceutical composition after storage at room temperature for greater than 365 days may be at least about 90% to about 110% (w/v) of the concentration of active ingredients that were initially present in the ophthalmic pharmaceutical formulation.

The ophthalmic pharmaceutical composition prepared by the disclosed method may include active ingredients such as a steroid, a non-steroidal anti-inflammatory agent, and a fluoroquinolone. In some aspects, the concentration of the steroid in the ophthalmic pharmaceutical composition after storage at room temperature for about 90 to 365 days may be at least about 90% to about 115% (w/v) of the concentration of the steroid that was initially present in the ophthalmic pharmaceutical formulation. In some additional aspects, the concentration of active ingredients in the ophthalmic pharmaceutical composition after storage at room temperature for about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days, may be at least 90%, 91%, 92%, 93%, 94%, 95%, 96%, 97%, 98%, 99%, 100%, 101%, 102%, 103%, 104% 105%, 106%, 107%, 108%, 109%, 110%, 111%, 112%, 113%, 114%, or 115% (w/v) of the concentration of active ingredients that was initially present in the ophthalmic pharmaceutical composition. In still further aspects, the concentration of active ingredients in the ophthalmic pharmaceutical composition after storage at room temperature for at least about 90, 100, 110, 120, 130, 140, 150, 160, 170, 180, 190, 200, 210, 220, 230, 240, 250, 260, 270, 280, 290, 300, 310, 320, 330, 340, 350, 360, or at least about 365 days, may be at least 90%, 91%, 92%, 93%, 94%, 95%, 96%, 97%, 98%, 99%, 100%, 101%, 102%, 103%, 104% 105%, 106%, 107%, 108%, 109%, 110%, 111%, 112%, 113%, 114%, or 115% (w/v) of the concentration of active ingredients that was initially present in the ophthalmic pharmaceutical composition. In preferred embodiments, the concentration of the steroid in the ophthalmic pharmaceutical composition after storage at room temperature for greater than 365 days may be at least about 90% to about 115% (w/v) of the concentration of active ingredients that were initially present in the ophthalmic pharmaceutical formulation.

The concentration of the non-steroidal anti-inflammatory agent in the ophthalmic pharmaceutical composition after storage at room temperature for about 90 to 365 days may be at least about 90% to about 110% (w/v) of the concentration of the steroid that was initially present in the ophthalmic pharmaceutical formulation. In some additional aspects, the concentration of active ingredients in the ophthalmic pharmaceutical composition after storage at room temperature for about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of active ingredients that was initially present in the ophthalmic pharmaceutical composition. In still further aspects, the concentration of active ingredients in the ophthalmic pharmaceutical composition after storage at room temperature for at least about 90, 100, 110, 120, 130, 140, 150, 160, 170, 180, 190, 200, 210, 220, 230, 240, 250, 260, 270, 280, 290, 300, 310, 320, 330, 340, 350, 360, or at least about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of active ingredients that was initially present in the ophthalmic pharmaceutical composition. In preferred embodiments, the concentration of the non-steroidal anti-inflammatory agent in the ophthalmic pharmaceutical composition after storage at room temperature for greater than 365 days may be at least about 90% to about 110% (w/v) of the concentration of active ingredients that were initially present in the ophthalmic pharmaceutical formulation.

The concentration of the fluoroquinolone in the ophthalmic pharmaceutical composition after storage at room temperature for about 90 to 365 days may be at least about 90% to about 110% (w/v) of the concentration of the steroid that was initially present in the ophthalmic pharmaceutical formulation. In some additional aspects, the concentration of active ingredients in the ophthalmic pharmaceutical composition after storage at room temperature for about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of active ingredients that was initially present in the ophthalmic pharmaceutical composition. In still further aspects, the concentration of active ingredients in the ophthalmic pharmaceutical composition after storage at room temperature for at least about 90, 100, 110, 120, 130, 140, 150, 160, 170, 180, 190, 200, 210, 220, 230, 240, 250, 260, 270, 280, 290, 300, 310, 320, 330, 340, 350, 360, or at least about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of active ingredients that was initially present in the ophthalmic pharmaceutical composition. In preferred embodiments, the concentration of the fluoroquinolone agent in the ophthalmic pharmaceutical composition after storage at room temperature for greater than 365 days may be at least about 90% to about 110% (w/v) of the concentration of active ingredients that were initially present in the ophthalmic pharmaceutical formulation.

In an exemplary embodiment, the ophthalmic pharmaceutical composition includes prednisolone acetate, bromfenac, and moxifloxacin hydrochloride. The concentration of the prednisolone acetate, bromfenac, and moxifloxacin hydrochloride in the ophthalmic pharmaceutical composition after storage at room temperature for about 90 to 365 days may be at least about 90% to about 110% (w/v) of the concentration of the steroid that was initially present in the ophthalmic pharmaceutical formulation. In some additional aspects, the concentration of prednisolone acetate, bromfenac, and moxifloxacin hydrochloride in the ophthalmic pharmaceutical composition after storage at room temperature for about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of prednisolone acetate, bromfenac, and moxifloxacin hydrochloride that was initially present in the ophthalmic pharmaceutical composition. In still further aspects, the concentration of prednisolone acetate, bromfenac, and moxifloxacin hydrochloride in the ophthalmic pharmaceutical composition after storage at room temperature for at least about 90, 100, 110, 120, 130, 140, 150, 160, 170, 180, 190, 200, 210, 220, 230, 240, 250, 260, 270, 280, 290, 300, 310, 320, 330, 340, 350, 360, or at least about 365 days, may be at least 90%, 91%, 92%, 93%, 94%, 95%, 96%, 97%, 98%, 99%, 100%, 101%, 102%, 103%, 104% 105%, 106%, 107%, 108%, 109%, or 110% (w/v) of the concentration of prednisolone acetate, bromfenac, and moxifloxacin hydrochloride that was initially present in the ophthalmic pharmaceutical composition. Preferably, the concentration of the prednisolone acetate, bromfenac, and moxifloxacin hydrochloride in the ophthalmic pharmaceutical composition after storage at room temperature for about greater than 365 days may be at least about 90% to about 110% (w/v) of the concentration of the steroid that was initially present in the ophthalmic pharmaceutical formulation.

In some aspects, the ophthalmic pharmaceutical composition has a pH from about 8.0 to about 8.5 when it is made. In some aspects, the pharmaceutical composition may have a pH from about 8.0 to about 8.1, about 8.0 to about 8.2, about 8.0 to about 8.3, about 8.0 to about 8.4, about 8.0 to about 8.5, about 8.1 to about 8.5, about 8.2 to about 8.5, about 8.3 to about 8.5, or about 8.4 to about 8.5. In some examples, the pharmaceutical composition may have a pH of about 8.0, 8.1, 8.2, 8.3, 8.4, or about 8.5 when it is made. In some additional examples, the pharmaceutical composition may have a pH between about 8.3 to about 8.5 when it is made.

In some embodiments, the ophthalmic pharmaceutical composition may have a pH of from about 7.5 and about 9.0 after about 90 days to about 365 days of storage at room temperature. In some aspects, the pH may be from about 7.5 to about 8.0, about 7.7 to about 8.2, about 8.0 to about 8.5, about 8.2 to about 8.7, or about 8.5 to about 9.0 after about 90 days to about 365 days of storage at room temperature. In some additional aspects, the ophthalmic composition may have a pH of about 7.5, 7.6, 7.7, 7.8, 7.9, 8.0, 8.1, 8.2, 8.3, 8.4, 8.5, 8.6, 8.7, 8.8, 8.9, or about 9.0 after about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days of storage at room temperature.

In still further aspects, the ophthalmic composition may have a pH of about 7.5, 7.6, 7.7, 7.8, 7.9, 8.0, 8.1, 8.2, 8.3, 8.4, 8.5, 8.6, 8.7, 8.8, 8.9, or about 9.0 after at least about 90, 100, 110, 120, 130, 140, 150, 160, 170, 180, 190, 200, 210, 220, 230, 240, 250, 260, 270, 280, 290, 300, 310, 320, 330, 340, 350, 360, or at least about 365 days of storage at room temperature. In some examples, the ophthalmic composition may have a pH of between about 8.3 to about 8.5 after about 90, 100, 110, 120, 130, 140, 150, 160, 170, 180, 190, 200, 210, 220, 230, 240, 250, 260, 270, 280, 290, 300, 310, 320, 330, 340, 350, 360, or about 365 days of storage at room temperature.

In some embodiments, autoclaving the first phase composition and the second phase composition may be accomplished at a temperature of about 121° C. In some embodiments, the pressure of the autoclave is between about 15 psi to about 18 psi. In some aspects, the autoclaving pressure may be about 15, 16, 17, or about 18 psi. In some embodiments, the first phase composition and/or the second phase composition may be autoclaved for at least about 30 minutes.

In additional embodiments, the second phase composition may be sterile-filtered as opposed to or in addition to autoclaving. Sterile-filtering may be accomplished by methods known in the art. In some embodiments when the second phase composition is autoclaved, the pressure of the autoclave is between about 15 psi to about 18 psi. In some aspects, the autoclaving pressure may be about 15, 16, 17, or about 18 psi. In some embodiments, the first phase composition and/or the second phase composition may be autoclaved for at least about 30 minutes.

The method further includes combining the first phase composition and the second phase composition. This step is performed aseptically to reduce the likelihood of contaminating the ophthalmic pharmaceutical composition. In some embodiments, combining the first phase composition and the second phase composition may include pouring the first phase composition and second phase composition into one or more sterilized vessel(s) to form a combined composition. The combined composition may additionally be aseptically mixed if needed.

The vessel(s) containing the combined composition may be sealed and packaged for consumer use, or may undergo further processing. In some embodiments, the vessels may be bottles that are equipped with a cap useful for dispensing single drops of the pharmaceutical ophthalmic composition. In some additional embodiments, the sealed vessel may undergo testing to ensure that it contains a predetermined volume of the ophthalmic pharmaceutical composition.

II. COMPOSITIONS

The method of the present disclosure may be used to extend the shelf-life of various sterile ophthalmic pharmaceutical compositions. The first phase composition may comprise a steroid and at least one excipient. The second phase composition may comprise a non-steroidal anti-inflammatory agent, a fluoroquinolone, and at least one excipient. In some aspects, the first phase composition and/or the second phase composition may be a suspension or an aqueous solution. In some additional aspects, the ophthalmic pharmaceutical composition may be a suspension or an aqueous solution.

(a) First Phase Composition

Steroid

An ophthalmic pharmaceutical composition made by the method described herein may include a steroid, such as a corticosteroid. In some embodiments, the corticosteroid may be dexamethasone, difluprednate, fluorometholone, loteprednol, prednisone, prednisolone, rimexolone, triamcinolone, or any other steroids known in the art or pharmaceutically acceptable salts thereof. In preferred embodiments, the corticosteroid is prednisolone acetate.

In some aspects, the steroid may have a concentration in the ophthalmic pharmaceutical composition of between about 0.2% (w/v) to about 1.5% (w/v). In some additional aspects, the steroid may have a concentration in the ophthalmic pharmaceutical composition of between about 0.4% (w/v) and about 1% (w/v), about 0.6% (w/v) and about 1% (w/v), or about 0.8% (w/v) and about 1% (w/v). In yet additional aspects, the steroid may have a concentration in the ophthalmic pharmaceutical composition of about 0.2% (w/v), 0.25% (w/v), 0.3% (w/v), 0.35% (w/v), 0.4% (w/v), 0.45% (w/v), 0.5% (w/v), 0.55% (w/v), 0.6% (w/v), 0.65% (w/v), 0.7% (w/v), 0.75% (w/v), 0.8% (w/v), 0.85% (w/v), 0.9% (w/v), 0.95% (w/v), or about 1% (w/v). In one example, the steroid is prednisolone acetate at a concentration of about 1% (w/v).

(b) Second Phase Composition (i) Non-Steroidal Anti-Inflammatory Agent

An ophthalmic pharmaceutical composition made by the method described herein may contain a non-steroidal anti-inflammatory agent in the second phase composition. In some embodiments, the non-steroidal anti-inflammatory agent may be diclofenac, ketorolac, bromfenac, etodolac, sulindac, aceclofenac, nepafenac, tolmetin, indomethacin, nabumetone, ketoprofen, dexketoprofen, ibuprofen, flurbiprofen, dexibuprofen, fenoprofen, loxoprofen, oxaprozin, naproxen, aspirin, salicylic acid, diflunisal, salsalate, mefenamic acid, meclofenamic acid, flufenamic acid, tolfenamic acid, meloxicam, piroxicam, ternoxicam, droxicam, lornoxicam, isoxicam, celecoxib, rofecoxib, valdecoxib, parecoxib, lumiracoxib, etoricoxib, firocoxib, nimesulide, clonixin, licofelone, or any other non-steroidal anti-inflammatory drug known in the art or pharmaceutically acceptable salts thereof.

In some aspects, the non-steroidal anti-inflammatory drug may have a concentration in the ophthalmic pharmaceutical composition of between about 0.05% (w/v) to about 0.5% (w/v). In some additional aspects, the concentration of the non-steroidal anti-inflammatory drug may have a concentration between about 0.05% (w/v) and about 0.4% (w/v), between about 0.05% (w/v) and about 0.3% (w/v), or between about 0.05% (w/v) and about 0.2% (w/v). In yet additional aspects, the non-steroidal anti-inflammatory drug may have a concentration in the ophthalmic pharmaceutical composition of about 0.05% (w/v), 0.075% (w/v) 0.1% (w/v), 0.125% (w/v), 0.15% (w/v), 0.175% (w/v), 0.2% (w/v), 0.225% (w/v), 0.25% (w/v), 0.275% (w/v), 0.3% (w/v), 0.325% (w/v), 0.35% (w/v), 0.375% (w/v), 0.4% (w/v), 0.425% (w/v), 0.45% (w/v), 0.475% (w/v), or about 0.5% (w/v). In one example, the non-steroidal anti-inflammatory drug is bromfenac at a concentration of about 0.075% (w/v).

(ii) Fluoroquinolone

An ophthalmic pharmaceutical composition made by the method described herein may contain a fluoroquinolone in the second phase composition. In some embodiments, the fluoroquinolone may be moxifloxacin, levofloxacin, ciprofloxacin, ofloxacin, gem ifloxacin, besifloxacin, gatifloxacin, delafloxacin, or other fluoroquinolones known in the art or pharmaceutically acceptable salts thereof. In one example, the fluoroquinolone is moxifloxacin.

In some aspects, the fluoroquinolone may have a concentration in the ophthalmic pharmaceutical composition of between about 0.3% (w/v) to about 1% (w/v). In some additional aspects, the fluoroquinolone may have a concentration in the ophthalmic pharmaceutical composition of between about 0.3% (w/v) to about 0.9% (w/v), between about 0.4% (w/v) to about 0.7% (w/v), or between about 0.45% (w/v) to about 0.55% (w/v). In yet additional aspects, the fluoroquinolone may have a concentration in the ophthalmic pharmaceutical composition of about 0.3% (w/v), 0.35% (w/v), 0.4% (w/v), 0.45% (w/v), 0.5% (w/v), 0.55% (w/v), 0.6% (w/v), 0.65% (w/v), 0.7% (w/v), 0.75% (w/v), 0.8% (w/v), 0.85% (w/v), 0.9% (w/v), 0.95% (w/v), or about 1% (w/v). In one example, the fluoroquinolone is moxifloxacin at a concentration of about 0.5% (w/v).

(c) Excipients

The first and second phases of the pharmaceutically-acceptable formulations may include pharmaceutically-acceptable excipients, including solvents, pH adjusting agents, buffering agents, antioxidants, tonicity modifying agents, osmotic adjusting agents, preservatives, antibacterial agents, stabilizing agents, viscosity adjusting agents, surfactants, or any other pharmaceutically-acceptable excipients known in the art or combinations thereof. Accordingly, the ophthalmic pharmaceutical composition of the present disclosure may include monosodium phosphate, disodium phosphate, sodium metabisulfite, sodium chloride, edetate disodium, potassium chloride, calcium chloride, sodium acetate, sodium citrate, sodium hydroxide, dextrose anhydrous, sodium bicarbonate, sodium borate, acetylcysteine, boric acid, citric acid, glycerin, monopotassium phosphate, dipotassium phosphate, hypromellose, polyethylene glycol 300, polyethylene glycol 400, carboxymethyl cellulose, hydroxyethyl cellulose, methylcellulose, polyoxyethylene sorbitan monooleate, dextran 70, polysorbate 80, methocel E4M, propylene glycol, gelatin, polyvinyl alcohol, povidone, benzalkonium chloride, or other pharmaceutically-acceptable excipients.

In some aspects, the excipients in the first phase composition or the second phase composition may be the same or they may be different. In one example, the excipients in the first phase composition may include sodium acetate, polyoxyethylene sorbitan monooleate, hypromellose, and any combination thereof, and the excipients in the second phase composition may include sodium phosphate, sodium metabisulfite, edetate disodium, boric acid, sodium borate, benzalkonium chloride, and any combination thereof.

In some embodiments, the composition may be preservative-free; i.e., the composition contains no preservatives or only trace amounts of preservatives.

III. EXEMPLARY EMBODIMENT

In one exemplary embodiment of an ophthalmic pharmaceutical composition created by the method disclosed herein, the steroid is prednisolone acetate at a concentration in the ophthalmic pharmaceutical composition of about 1% (w/v), the non-steroidal anti-inflammatory drug is bromfenac at a concentration in the ophthalmic pharmaceutical composition of about 0.075% (w/v), and the fluoroquinolone is moxifloxacin at a concentration in the ophthalmic pharmaceutical composition of about 0.5% (w/v). Additionally, the excipients in the first phase composition are sodium acetate, polyoxyethylene sorbitan monooleate, and hypromellose, and the excipients in the second phase composition are sodium phosphate, sodium metabisulfite, edetate disodium, boric acid, sodium borate, and benzalkonium chloride. The ophthalmic pharmaceutical composition has a pH of between about 8.3-8.5 when made. After at least 300 days of storage at room temperature, the concentration of the prednisolone acetate in the ophthalmic pharmaceutical composition is about 100% of the original concentration of prednisolone acetate, the concentration of bromfenac in the ophthalmic pharmaceutical composition is about 100% of the original concentration of bromfenac, the concentration of moxifloxacin in the ophthalmic pharmaceutical composition is about 100% of the original concentration of moxifloxacin, and the pH of the ophthalmic pharmaceutical composition is between about 7.8 and about 9.0.

EXAMPLES

Example 1

The stability of an ophthalmic pharmaceutical composition made by the method of the present disclosure was studied and confirmed by the Compounder's International Analytical Laboratory. The data collected included the concentration of the active ingredients in the composition, the pH, and the appearance, color, and odor of the composition. The amount of active ingredient in the ophthalmic pharmaceutical composition was determined by ultra high performance liquid chromatography (UHPLC). The composition was stored at 25° C. The composition comprised the active ingredients bromfenac, moxifloxacin, and prednisolone acetate. The composition was considered stable if it contained 90-110% of the label claim of bromfenac and moxifloxacin and 90-115% of the label claim of prednisolone acetate.

A sample of the composition was provided on Jul. 31, 2020. Table 1 shows the baseline stability data gathered on Aug. 21, 2020.

TABLE 1

| | | | | Baseline Stability Data | | | | |
|---|---|---|---|---|---|---|---|---|
| Active Ingredient | Label Claim | Acceptance Criteria | Amount Found | % Label Claim | Pass/ Fail | pH | Appearance, Odor, and Color | |
| Bromfenac | 0.075% | 90-110% | 0.08023% | 107.0% | Pass | 8.50 | Liquid sample in good |
| Moxifloxacin | 0.5% | 90-110% | 0.5043% | 100.9% | Pass | | condition. Opaque, |
| Prednisolone acetate | 1% | 90-115% | 1.000% | 100.0% | Pass | | yellow suspension with water viscosity that forms persistent bubbles when shaken. No apparent odor. |

The next stability tests were conducted at 90 days after the baseline test on Nov. 11, 2020. Table 2 shows the 90-day stability data.

TABLE 2

| | | | | Stability Data After 90 Days | | | | |
|---|---|---|---|---|---|---|---|---|
| Active Ingredient | Label Claim | Acceptance Criteria | Amount Found | % Label Claim | Pass/ Fail | pH | Appearance, Odor, and Color | |
| Bromfenac | 0.075% | 90-110% | 0.07373% | 98.3% | Pass | 8.44 | Liquid sample in good condition. Opaque, yellow suspension with water viscosity that forms persistent bubbles when shaken. No apparent odor. | |
| Moxifloxacin | 0.5% | 90-110% | 0.4888% | 97.8% | Pass | | | |
| Prednisolone acetate | 1% | 90-115% | 0.9915% | 99.2% | Pass | | | |

The next stability tests were conducted at 120 days after the baseline test on Dec. 14, 2020. Table 3 shows the 120-day stability data.

TABLE 3

| | | | | Stability Data After 120 Days | | | | |
|---|---|---|---|---|---|---|---|---|
| Active Ingredient | Label Claim | Acceptance Criteria | Amount Found | % Label Claim | Pass/ Fail | pH | Appearance, Odor, and Color | |
| Bromfenac | 0.075% | 90-110% | 0.07559% | 100.8% | Pass | 8.33 | Liquid sample in good condition. Opaque, yellow suspension with water viscosity that forms persistent bubbles when shaken. No apparent odor. | |
| Moxifloxacin | 0.5% | 90-110% | 0.4949% | 99.0% | Pass | | | |
| Prednisolone acetate | 1% | 90-115% | 1.035% | 103.5% | Pass | | | |

The next stability tests were conducted 180 days after the baseline test on Feb. 8, 2021. Table 4 shows the 180-day stability data.

TABLE 4

| | | | | Stability Data After 180 Days | | | | |
|---|---|---|---|---|---|---|---|---|
| Active Ingredient | Label Claim | Acceptance Criteria | Amount Found | % Label Claim | Pass/ Fail | pH | Appearance, Odor, and Color | |
| Bromfenac | 0.075% | 90-110% | 0.07917% | 105.6% | Pass | 8.40 | Liquid sample in good condition. Opaque, yellow suspension with water viscosity that forms persistent bubbles when shaken. No apparent odor. | |
| Moxifloxacin | 0.5% | 90-110% | 0.5107% | 102.1% | Pass | | | |
| Prednisolone acetate | 1% | 90-115% | 1.056% | 105.6% | Pass | | | |

The next stability tests were conducted 210 days after the baseline test on Mar. 9, 2021. Table 5 shows the 210-day stability data.

TABLE 5

| | | | | Stability Data After 210 Days | | | | |
|---|---|---|---|---|---|---|---|---|
| Active Ingredient | Label Claim | Acceptance Criteria | Amount Found | % Label Claim | Pass/ Fail | pH | Appearance, Odor, and Color | |
| Bromfenac | 0.075% | 90-110% | 0.07620% | 101.6% | Pass | 8.31 | Liquid sample in good condition. Opaque, | |
| Moxifloxacin | 0.5% | 90-110% | 0.4948% | 99.0% | Pass | | | |

TABLE 5-continued

| | | | | % | | | |
|---|---|---|---|---|---|---|---|
| | | | | Stability Data After 210 Days | | | |
| Active Ingredient | Label Claim | Acceptance Criteria | Amount Found | Label Claim | Pass/ Fail | pH | Appearance, Odor, and Color |
| Prednisolone acetate | 1% | 90-115% | 1.065% | 106.5% | Pass | | yellow suspension with water viscosity that formed persistent bubbles when shaken. No apparent odor. |

The next stability tests were conducted 270 days after the baseline test on May 12, 2021. Table 6 shows the 270-day stability data.

TABLE 6

| | | | | % | | | |
|---|---|---|---|---|---|---|---|
| | | | | Stability Data After 270 Days | | | |
| Active Ingredient | Label Claim | Acceptance Criteria | Amount Found | Label Claim | Pass/ Fail | pH | Appearance, Odor, and Color |
| Bromfenac | 0.075% | 90-110% | 0.07312% | 97.5% | Pass | 8.33 | Liquid sample in good |
| Moxifloxacin | 0.5% | 90-110% | 0.4974% | 99.5% | Pass | | condition. Opaque, dark |
| Prednisolone acetate | 1% | 90-115% | 1.036% | 103.6% | Pass | | yellow suspension with formed persistent bubbles when shaken. No apparent odor. |

Example 2

The stability of an ophthalmic pharmaceutical composition made by the method of the present disclosure was studied and confirmed by the Compounder's International Analytical Laboratory. The data collected included the concentration of the active ingredients in the composition, the pH, and the appearance, color, and odor of the composition. The amount of active ingredient in the ophthalmic pharmaceutical composition was determined by ultra high performance liquid chromatography (UHPLC). The composition was stored at 25° C. The composition comprised the active ingredients bromfenac, moxifloxacin, and prednisolone acetate. The composition was considered stable if it contained 90-110% of the label claim of bromfenac and moxifloxacin and 90-115% of the label claim of prednisolone acetate. pH was determined according to USP 791, incorporated by reference herein. Additionally, the container enclosure was tested at baseline according to USP 1207 and 381, incorporated by reference herein. No blue dye was observed via UV-Vis spectrophotometry.

A sample of the composition was provided on May 28, 2021. Table 7 shows the baseline stability data gathered on Jun. 7, 2021.

TABLE 7

| | | | | % | | | |
|---|---|---|---|---|---|---|---|
| | | | | Baseline Stability Data | | | |
| Active Ingredient | Label Claim | Acceptance Criteria | Amount Found | Label Claim | Pass/ Fail | pH | Appearance, Odor, and Color |
| Bromfenac | 0.075% | 90-110% | 0.07499% | 100.0% | Pass | 8.13 | Liquid sample in good |
| Moxifloxacin | 0.5% | 90-110% | 0.4835% | 96.7% | Pass | | condition. Opaque, |
| Prednisolone acetate | 1% | 90-115% | 1.024% | 102.4% | Pass | | yellow suspension with water viscosity that forms persistent bubbles when shaken. No apparent odor. |

The next stability tests were conducted at 90 days after the baseline test on Sep. 3, 2021. Table 8 shows the 90-day stability data.

TABLE 8

| | | | | Stability Data After 90 Days | | | |
| Active Ingredient | Label Claim | Acceptance Criteria | Amount Found | % Label Claim | Pass/ Fail | pH | Appearance, Odor, and Color |
|---|---|---|---|---|---|---|---|
| Bromfenac | 0.075% | 90-110% | 0.07646% | 101.9% | Pass | 7.88 | Liquid sample in good condition. Opaque, yellow suspension with water viscosity that forms persistent bubbles when shaken. No apparent odor. |
| Moxifloxacin | 0.5% | 90-110% | 0.5039% | 100.8% | Pass | | |
| Prednisolone acetate | 1% | 90-115% | 0.9805% | 98.0% | Pass | | |

The next stability tests were conducted at 180 days after the baseline test on Dec. 1, 2021. Table 9 shows the 180-day stability data.

TABLE 9

| | | | | Stability Data After 180 Days | | | |
| Active Ingredient | Label Claim | Acceptance Criteria | Amount Found | % Label Claim | Pass/ Fail | pH | Appearance, Odor, and Color |
|---|---|---|---|---|---|---|---|
| Bromfenac | 0.075% | 90-110% | 0.07398% | 98.6% | Pass | 7.83 | Liquid sample in good condition. Opaque, yellow suspension with water viscosity that forms persistent bubbles when shaken. No apparent odor. |
| Moxifloxacin | 0.5% | 90-110% | 0.4816% | 96.3% | Pass | | |
| Prednisolone acetate | 1% | 90-115% | 0.9883% | 98.8% | Pass | | |

The next stability tests were conducted 270 days after the baseline test on Mar. 1, 2022. Table 10 shows the 270-day stability data.

TABLE 10

| | | | | Stability Data After 270 Days | | | |
| Active Ingredient | Label Claim | Acceptance Criteria | Amount Found | % Label Claim | Pass/ Fail | pH | Appearance, Odor, and Color |
|---|---|---|---|---|---|---|---|
| Bromfenac | 0.075% | 90-110% | 0.06939% | 92.5% | Pass | 7.79 | Liquid sample in good condition. Opaque, yellow suspension with water viscosity that forms persistent bubbles when shaken. No apparent odor. |
| Moxifloxacin | 0.5% | 90-110% | 0.4813% | 96.3% | Pass | | |
| Prednisolone acetate | 1% | 90-115% | 0.9743% | 97.4% | Pass | | |

The next stability tests were conducted 300 days after the baseline test on Apr. 14, 2022. Table 11 shows the 300-day stability data.

TABLE 11

| | | | | Stability Data After 300 Days | | | |
| Active Ingredient | Label Claim | Acceptance Criteria | Amount Found | % Label Claim | Pass/ Fail | pH | Appearance, Odor, and Color |
|---|---|---|---|---|---|---|---|
| Bromfenac | 0.075% | 90-110% | 0.07160% | 95.5% | Pass | 7.80 | Liquid sample in good condition. Opaque, yellow suspension with water viscosity that formed persistent |
| Moxifloxacin | 0.5% | 90-110% | 0.5060% | 101.2% | Pass | | |
| Prednisolone acetate | 1% | 90-115% | 0.9954% | 99.5% | Pass | | |

TABLE 11-continued

| | | | | % | | | |
|---|---|---|---|---|---|---|---|
| Active Ingredient | Label Claim | Acceptance Criteria | Amount Found | Label Claim | Pass/ Fail | pH | Appearance, Odor, and Color |

_Stability Data After 300 Days_

| | | | | | | | bubbles when shaken. No apparent odor. |

The next stability tests were conducted 365 days after the baseline test on Jun. 6, 2022. Table 12 shows the 365-day stability data.

TABLE 12

_Stability Data After 365 Days_

| Active Ingredient | Label Claim | Acceptance Criteria | Amount Found | % Label Claim | Pass/ Fail | pH | Appearance, Odor, and Color |
|---|---|---|---|---|---|---|---|
| Bromfenac | 0.075% | 90-110% | 0.06834% | 91.1% | Pass | 7.80 | Liquid sample in good |
| Moxifloxacin | 0.5% | 90-110% | 0.4952% | 99.0% | Pass | | condition. Opaque, |
| Prednisolone acetate | 1% | 90-115% | 0.9960% | 99.6% | Pass | | yellow suspension that formed persistent bubbles when shaken. No apparent odor. |

Example 3

The stability of a composition made by mixing all ingredients together an autoclaving the batch (the "comparator composition") was studied and confirmed by the Compounder's International Analytical Laboratory. The data collected included the concentration of the active ingredients in the composition. The amount of active ingredient in the composition was determined by ultra high performance liquid chromatography (UHPLC). The comparator composition was stored at 25° C. The composition comprised the active ingredients bromfenac, moxifloxacin, and prednisolone acetate. The comparator composition was considered stable if it contained 90-110% of the label claim of bromfenac and moxifloxacin and 90-115% of the label claim of prednisolone acetate.

A sample of the composition was provided on Nov. 17, 2017. Table 13 shows the baseline stability data gathered on Dec. 6, 2017. The pH of the comparator composition at baseline was 7.005.

TABLE 13

_Baseline Stability Data (Comparator Composition)_

| Active Ingredient | Label Claim | Acceptance Criteria | Amount Found | % Label Claim (Potency) | Pass/Fail |
|---|---|---|---|---|---|
| Bromfenac | 0.075% | 90-110% | 0.0747% | 99.6% | Pass |
| Moxifloxacin | 0.5% | 90-110% | 0.491% | 98.2% | Pass |
| Prednisolone acetate | 1% | 90-115% | 0.984% | 98.4% | Pass |

The next stability tests were conducted 30 days after the baseline test on Jan. 9, 2018. Table 14 shows the 30-day stability data.

TABLE 14

_Stability Data after 30 Days (Comparator Composition)_

| Active Ingredient | Label Claim | Acceptance Criteria | Amount Found | % Label Claim (Potency) | Pass/Fail |
|---|---|---|---|---|---|
| Bromfenac | 0.075% | 90-110% | 0.071% | 94.9% | Pass |
| Moxifloxacin | 0.5% | 90-110% | 0.480% | 96.0% | Pass |
| Prednisolone acetate | 1% | 90-115% | 0.978% | 97.8% | Pass |

The next stability tests were conducted 60 days after the baseline test on Feb. 6, 2018. Table 15 shows the 60-day stability data.

TABLE 15

_Stability Data after 60 Days (Comparator Composition)_

| Active Ingredient | Label Claim | Acceptance Criteria | Amount Found | % Label Claim (Potency) | Pass/Fail |
|---|---|---|---|---|---|
| Bromfenac | 0.075% | 90-110% | 0.0692% | 92.2% | Pass |
| Moxifloxacin | 0.5% | 90-110% | 0.4989% | 99.8% | Pass |
| Prednisolone acetate | 1% | 90-115% | 0.9001% | 90.0% | Pass |

The next stability tests were conducted 90 days after the baseline test on Mar. 23, 2018. Table 16 shows the 90-day stability data.

TABLE 16

_Stability Data after 90 Days (Comparator Composition)_

| Active Ingredient | Label Claim | Acceptance Criteria | Amount Found | % Label Claim (Potency) | Pass/Fail |
|---|---|---|---|---|---|
| Bromfenac | 0.075% | 90-110% | 0.0660% | 87% | Fail |
| Moxifloxacin | 0.5% | 90-110% | 0.4876% | 98% | Pass |

TABLE 16-continued

| Stability Data after 90 Days (Comparator Composition) | | | | |
|---|---|---|---|---|
| Active Ingredient | Label Claim | Acceptance Criteria | Amount Found | % Label Claim (Potency) | Pass/Fail |
| Prednisolone acetate | 1% | 90-115% | 0.9885% | 99% | Pass |

The next stability tests were conducted 120 days after the baseline test on Apr. 13, 2018. Table 17 shows the 120-day stability data.

TABLE 17

| Stability Data after 120 Days (Comparator Composition) | | | | | |
|---|---|---|---|---|---|
| Active Ingredient | Label Claim | Acceptance Criteria | Amount Found | % Label Claim (Potency) | Pass/Fail |
| Bromfenac | 0.075% | 90-110% | 0.0618% | 82% | Fail |
| Moxifloxacin | 0.5% | 90-110% | 0.4961% | 99% | Pass |
| Prednisolone acetate | 1% | 90-115% | 0.9505% | 95% | Pass |

The next stability tests were conducted 150 days after the baseline test on May 9, 2018. Table 18 shows the 150-day stability data.

TABLE 18

| Stability Data after 150 Days (Comparator Composition) | | | | | |
|---|---|---|---|---|---|
| Active Ingredient | Label Claim | Acceptance Criteria | Amount Found | % Label Claim (Potency) | Pass/Fail |
| Bromfenac | 0.075% | 90-110% | 0.0627% | 84% | Fail |
| Moxifloxacin | 0.5% | 90-110% | 0.482% | 96% | Pass |
| Prednisolone acetate | 1% | 90-115% | 0.926% | 93% | Pass |

The next stability tests were conducted 180 days after the baseline test on Jun. 4, 2018. Table 19 shows the 180-day stability data. The pH on day 180 was measured to be 6.90.

TABLE 19

| Stability Data after 180 Days (Comparator Composition) | | | | | |
|---|---|---|---|---|---|
| Active Ingredient | Label Claim | Acceptance Criteria | Amount Found | % Label Claim (Potency) | Pass/Fail |
| Bromfenac | 0.075% | 90-110% | 0.0584% | 78% | Fail |
| Moxifloxacin | 0.5% | 90-110% | 0.487% | 97% | Pass |
| Prednisolone acetate | 1% | 90-115% | 0.907% | 91% | Pass |

As can be seen from the 180-day stability data, the potency of the comparator composition is falls outside the acceptable range on day 90.

Example 4

A sterile, ophthalmic pharmaceutical composition was prepared as described below. The following products were used in the amounts and concentrations specified.

(a) about 75.0 g of prednisolone acetate, USP Micronized,
(b) about 37.5 g of moxifloxacin hydrochloride, USP, (c) about 5.625 g of bromfenac,
(d) about 0.75 g of edetate disodium, USP,
(e) about 7.5 g of sodium acetate, USP,
(f) about 15.0 g of boric acid, NF,
(g) about 5.625 g of sodium borate, NF,
(h) about 3.75 g of sodium metabisulfite, NF,
(i) about 3.0 g of sodium phosphate monobasic anhydrous,
(j) about 7.5 mL of Polysorbate 80, NF liquid,
(k) about 1.5 mL of benzalkonium chloride solution, NF 50%,
(l) about 15.0 g Methocel E4M,
(m) q.s. water for injection to 7,500 g,
(n) hydrochloric acid and/or sodium hydroxide as needed to adjust pH.

A 3 L de-pyrogenated mixing vessel was obtained, to which 2500 g of water for injection was added. A SERVO-DYNE mixer was lowered into the vessel. The mixer began mixing at a speed of 500±350 rpm.

Next, the first phase composition was made. The sodium acetate, Polysorbate 80, prednisolone acetate, and Methocel E4M, were measured and added to the mixing vessel one-by-one. Each ingredient was allowed to dissolve before the next ingredient was added. The prednisolone acetate and Methocel E4M were sprinkled slowly into the vessel to avoid clumping. Mixing continued for about 15 more minutes, and then the pH of the solution was measured. Water for injection was then added to qs the batch to 3000 g. The vessel was then mixed for about another 10 minutes.

Two sterilized pyrex bottles, two autoclaved magnetic spinning bars, and a sterilized funnel were then provided. The first phase composition was then transferred into the two sterilized pyrex bottles. The vessel was then rinsed with water for injection, with the rinse being added to each pyrex bottle.

Next, the second phase composition was made. Another de-pyrogenated 3 L mixing vessel was provided, to which 2,500 g of water for injection was added. A clean SERVO-DYNE mixer was provided and lowered into the mixing vessel. The mixer began mixing at a speed of 500±350 rpm.

The sodium phosphate monobasic anhydrous, sodium metabisulfite, edetate disodium, boric acid, sodium borate, benzalkonium chloride, and moxifloxacin hydrochloride were each measured and added one-by-one. After all ingredients had dissolved completely, the pH of the solution was recorded. Sodium hydroxide was added as needed to bring the solution to a pH of 8.3-8.5. Next, the bromfenac was measured and added slowly to the mixing vessel to avoid clumping. The bromfenac was allowed to dissolve completely before the pH was measured again. Sodium hydroxide and/or hydrochloric acid were added as needed to bring the pH to between 8.3-8.5. Water for injection was added to the vessel to qs the batch to 3,000 g.

Three sterile pyrex bottles, two autoclaved magnetic spinning bars, and a sterile funnel were provided. The second phase composition was then transferred into two of the sterilized pyrex bottles using the sterile funnel. In the $3^{rd}$ pyrex bottle, 1,500 g of water for injection was added. A magnetic spinning bar was added to each bottle. The vessel was then rinsed with water for injection, with the rinse being added to each pyrex bottle.

Next, the two pyrex bottles containing the first phase composition were placed inside an autoclave. The first phase composition was autoclaved for 30 minutes at 121° C. and 15-18 psi. The two pyrex bottles containing the second phase composition and the pyrex bottle containing the water for injection were placed inside a second autoclave. The second phase composition and the water for injection were autoclaved for 30 minutes at 121° C. and 15-18 psi.

After the bottles were autoclaved, the bottles containing the first phase composition and second phase composition were placed on mixing plates. The speed was adjusted to stir the contents. The contents of all four bottles were then transferred to a 10 L de-pyrogenated glass bottle using aseptic technique. The bottles were rinsed with the auto-claved water for injection, and the contents were added to the 10 L bottle and mixed.

The contents of the 10 L bottle were then transferred to 10 mL screw-cap bottles.

What is claimed is:

1. A method for extending the shelf life of a sterile, preservative-free, ophthalmic pharmaceutical composition, the method comprising:
   autoclaving a first phase composition consisting of pred-nisolone or a pharmaceutically acceptable salt thereof, sodium acetate, sodium chloride polyoxyethylene sor-bitan monooleate, hydroxypropyl methylcellulose, optionally hydrochloric acid, optionally sodium hydroxide, and water;
   autoclaving or sterile filtering a second phase composition consisting of moxifloxacin, bromfenac, sodium phos-phate, sodium metabisulfite, edetate disodium, boric acid, sodium borate, optionally hydrochloric acid, optionally sodium hydroxide, and water; and
   combining the first phase composition and the second phase composition, aseptically,
   wherein the ophthalmic pharmaceutical composition has a shelf life that is at least 90 days when stored at room temperature.

2. The method of claim 1, wherein the autoclaving tem-perature is about 121° C.

3. The method of claim 1, wherein the autoclaving pres-sure is about 15 psi to about 18 psi.

4. The method of claim 1, wherein the first phase com-position is autoclaved for about 30 minutes.

5. The method of claim 1, wherein the second phase composition is autoclaved for about 30 minutes.

6. The method of claim 1, wherein the shelf life of the ophthalmic pharmaceutical composition is at least 120 days when stored at room temperature.

7. The method of claim 6, wherein the shelf life of the ophthalmic pharmaceutical composition is at least 180 days when stored at room temperature.

8. The method of claim 7, wherein the shelf life of the ophthalmic pharmaceutical composition is at least 240 days when stored at room temperature.

9. The method of claim 8, wherein the shelf life of the ophthalmic pharmaceutical composition is at least 270 days when stored at room temperature.

10. The method of claim 9, wherein the shelf life of the pharmaceutical composition is at least 300 days when stored at room temperature.

11. The method of claim 10, wherein the shelf life of the ophthalmic pharmaceutical composition is at least 365 days when stored at room temperature.

12. The method of claim 1, wherein the ophthalmic pharmaceutical composition has a pH of between about 7.5 to about 9.0.

13. The method of claim 12, wherein the ophthalmic pharmaceutical composition has a pH of between about 8.3 to about 8.5.

* * * * *